United States Patent [19]

Lubineau et al.

[11] Patent Number: 5,169,943

[45] Date of Patent: Dec. 8, 1992

[54] CHIRAL REACTION MEDIUM FOR ORGANIC REACTIONS

[75] Inventors: André Lubineau, Dourdan; Hugues Bienayme, Paris; Yves Queneau, Boulogne Billancourt, all of France

[73] Assignee: Beghin-Say, S.A., Thumeries, France

[21] Appl. No.: 623,707

[22] PCT Filed: Apr. 12, 1990

[86] PCT No.: PCT/FR90/00267

§ 371 Date: Dec. 14, 1990

§ 102(e) Date: Dec. 14, 1990

[87] PCT Pub. No.: WO90/12773

PCT Pub. Date: Nov. 1, 1990

[30] Foreign Application Priority Data

Apr. 14, 1989 [FR] France ................. 89 04950

[51] Int. Cl.⁵ ............ C08B 37/00; C07H 1/00; C07H 3/00
[52] U.S. Cl. .................. 536/124; 106/162; 536/1.1; 568/338; 568/383; 568/426; 568/449; 568/950

[58] Field of Search .............. 106/162; 127/2, 9; 514/23; 536/124; 568/338, 383, 426, 449, 950

[56] References Cited

U.S. PATENT DOCUMENTS 4,144,261 3/1979 Chan ................. 562/804

OTHER PUBLICATIONS

Manuel of Medical Therapeutics, 23rd Edition, Freitag et al. editors, Department of Medicine, Washington University School of Medicine, St. Louis, Missouri, Little Brown and Company Boston, Mass. (1980), p. 401.

Primary Examiner—Ronald W. Griffin
Attorney, Agent, or Firm—Breiner & Breiner

[57] ABSTRACT

The invention concerns a chiral reaction medium for organic reactions and consists of concentrated aqueous solution of at least one carbohydrate selected from among the mono-, di- and tri-saccharides and their alkylglucosides of which the alkyl group comprises from 1 to 4 C atoms.

2 Claims, 1 Drawing Sheet

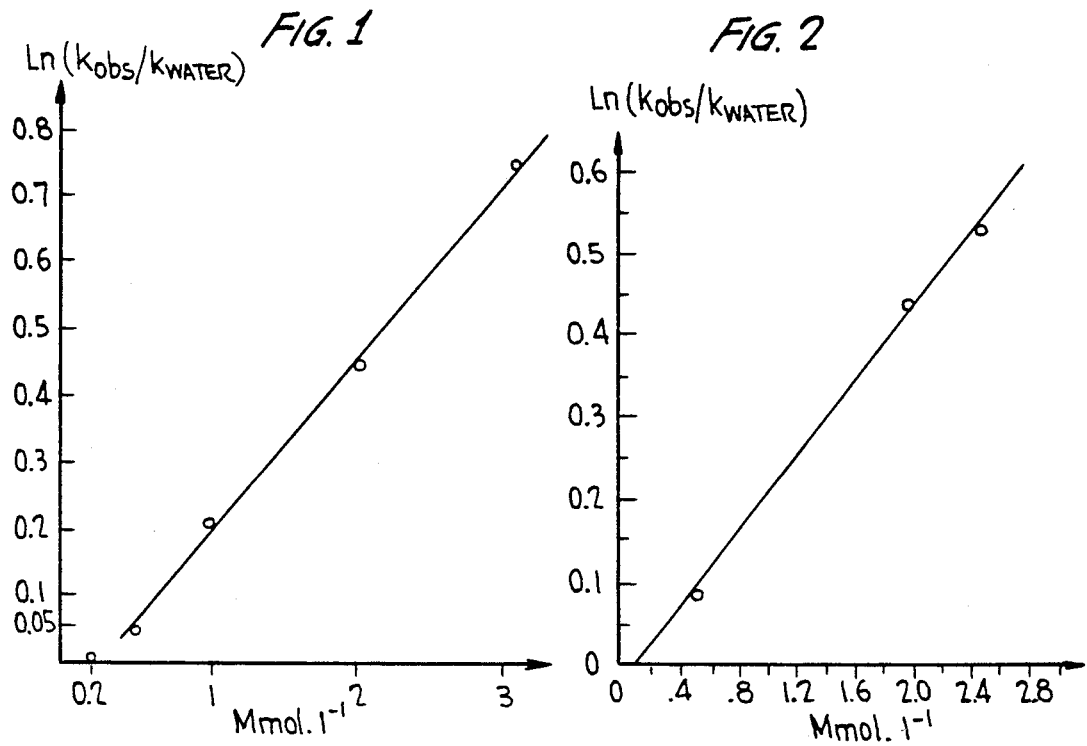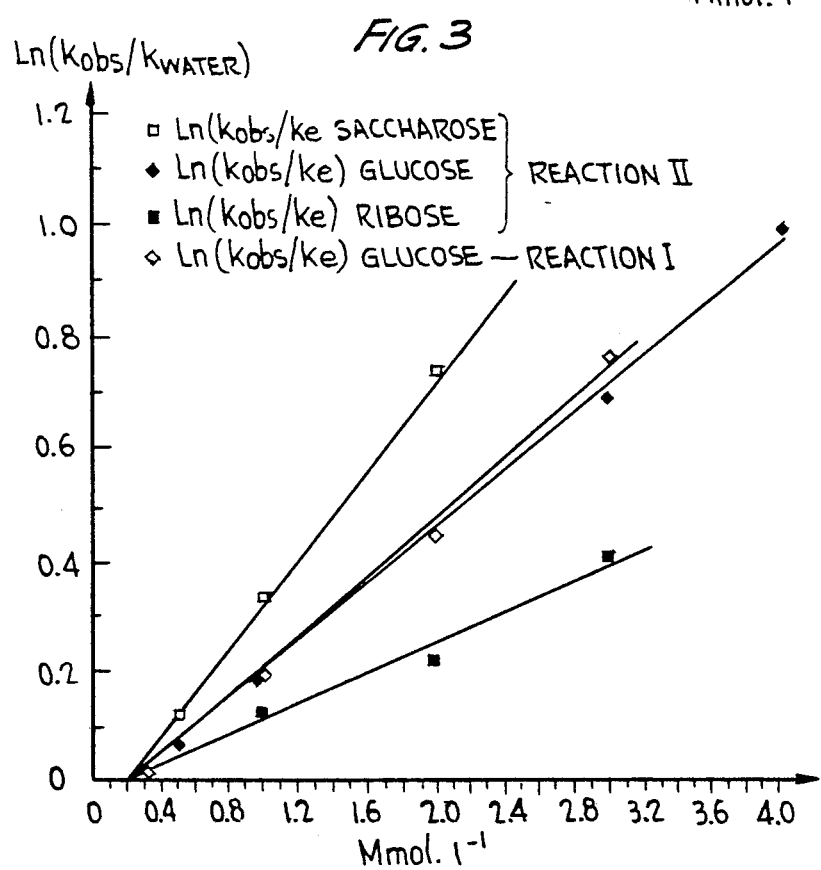

CHIRAL REACTION MEDIUM FOR ORGANIC REACTIONS

DESCRIPTION

The present invention concerns a novel chiral reaction medium for organic reactions.

There is widespread need in industry to optimize organic reactions and research is constantly undertaken to that end. Much work has been done in particular on increasing the reaction rates. Such increase in reaction rate most of the time has been possible only by resorting to catalyst(s) and/or to high pressures, entailing steps which are costly and/or difficult to carry out. Again frequently the use of organic solvents has been advocated, where called for in combination with other steps such as those cited above, but besides the generally high, even prohibitive cost of such solvents, their use raises problems because of their toxicity.

Again there is widespread industrial need to control the selectivity of organic reactions, in particular the regio-selectivity, the stereo-selectivity, the enantio-selectivity and the chemo-selectivity. Various solutions already have been suggested in this respect in relation to the particular problem to be solved, and among these is the use of chiral solvents, however the latter's cost is so high that processes involving reactions carried out in such solvents are economically of little interest.

The present invention provides a reaction medium which makes it possible to substantially increase the rates of organic reactions and where called for to modify their selectivities while palliating the aforementioned difficulties.

Accordingly the present invention provides an organic reaction medium consisting of a concentrated aqueous solution of at least one carbohydrate selected among the mono-, di- and tri-saccharides and their alkylglycosides of which the alkyl group comprises from 1 to 4 carbon atoms.

In illustrative but non restrictive manner, the carbohydrates applicable within the present invention are glucose, fructose, saccharose, ribose, galactose, mannose, α-methyl-glucoside.

The expression "concentrated solution" means a solution with a concentration at least about 0.2 M; this value however is not critical and the lower concentration limit of said carbohydrate is easily determined by the expert for the particular reaction being considered.

The present invention shall now be discussed comprehensively with particular reference to the Diels-Alder reactions, but it must be borne in mind that the illustration provided by this sort of reaction is merely illustrative both of the unexpected character of the invention and some advantages it may provide, no restriction of its scope being in any way implied.

It is known that the Diels-Alder reactions are considerably accelerated in water as compared to organic solvents (see RIDEOUT, D. C., BRESLOW, R. J. AM. CHEM. SOC. 1980, 102, 7816; GRIECO, P. A.; YOSHIDA, K., GARNER, P. J. ORG. CHEM. 1983, 48, 3139 and LUBINEAU, A., QUENEAU, Y., J. ORG. CHEM. 1987, 52, 1001).

It is further known that cyclodextrin β accelerates Diels-Alder reactions in an aqueous medium by forming hydrophobic diene and dienophil accumulation inside its hydrophobic cage (Rideout, D. C., Breslow, R. J. AM. CHEM. SOC. 1980, 102, 7816, LOC. CIT., and STERNBACH, D. D., ROSSANA, D. M. J. AM. CHEM. SOC. 1982, 104, 5853).

The cyclodextrins are carbohydrates but contrary to the case of the mono-, di- and tri-saccharides used in the present invention, they consist of 6, 7 or 8 glucose units forming a ring which comprises at its center a hydrophobic cage.

Aqueous solutions of mono-, di- and tri-saccharides not being known to form such cages, it might be expected that acceleration in such medium would be much less than in a reaction medium consisting of a saturated solution of said cyclodextrin.

Surprisingly the applicant found not only that aqueous solutions of carbohydrates selected among the mono-, di- and tri-saccharides and their alkylglycosides wherein the alkyl group comprises from 1 to 4 C atoms constitute a reaction medium allowing an increase in the rate of organic reactions, but also that the acceleration so obtained may even be significantly higher than that provided by a saturated aqueous cyclodextrin solution, as shown by the non-restrictive Examples below.

The chiral reaction medium of the present invention illustratively may be used to carry out all cyclo-additions, for instance the Diels-Alder reactions, photochemical cyclo-additions in photochemistry for instance to achieve photo-Smiles rearrangements, asymmetric inductions in reduction reactions, regio-selective functionalizations of aromatic compounds (hydroxymethylation, chlorination, iodation etc.), aldol condensations, asymmetric epoxidations, ester hydrolysis using lipophilic chains, in organo-metal chemistry of the transition elements, oxidation of olefins (especially by the Wacker method).

EXAMPLES

Examples 1 through 3 below concern the Diels-Alder reaction between 1-β-D-glucosyl-1,3-butadiene and butenone at 25° C. at atmospheric pressure in aqueous reaction media. The 1-β-D-glucosyl-1,3-butadiene of formula 1 shown below

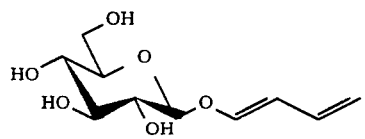

was prepared as indicated in the above cited publication LUBINEAU A., QUENEAU, Y. J. ORG. CHEM. 1987, 52, 1001.

This preparation method is as follows:

PREPARING 1β-D-GLUCOSYL-1,3-BUTADIENE (DIENE 1)

(a) Easily available acetobromoglucose 2 was treated in a solution of Me$_2$SO with the salt of sodium malonaldehyde. Aldehyde 3 was obtained which was isolated by direct crystallization with a yield of 56%. The reaction is the following

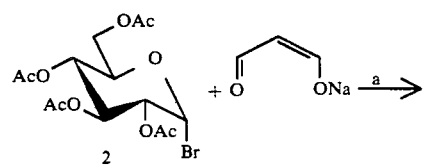

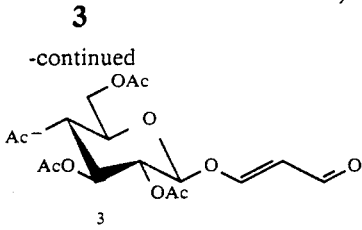

3

As shown in the publication by DAVID, S.; LUBINEAU, A.,; VATELE, J. M., NOUV. J. CHIM. 1980, 4, 547, the addition (b) of "salt-free" methylene triphenylphosphorane to aldehyde 3 at −78° C. in a mixture of oxolane-toluene results in β configuration diene 4 at a yield of 83%. Deacetylation (c) in a mixture of NET$_3$—MeOH—H$_2$O (1:8:1) results in diene 1 at a nearly quantitative yield. The reaction is as follows

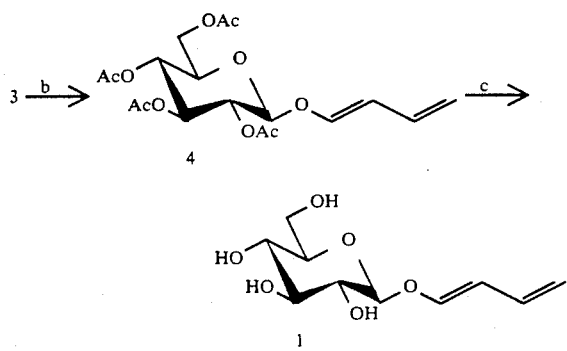

Example 1

In this Example, the Diels-Alder reaction between 1-β-D-glucosyl-1,3-butadiene (1) and butenone (5) [reaction (I)] is carried out at 25° C. and at atmospheric pressure in pure water (comparison test 1), in an aqueous solution of MeOH at 50% (comparison test 2), in 0.5 M aqueous glucose solutions, in 1 M aqueous glucose solutions, in 2 M aqueous glucose solutions, in 3 M aqueous glucose solutions, in 0.5 M aqueous saccharose solutions, in 2 M ribose aqueous solutions, in 1 M mannose aqueous solutions, in 1 M aqueous galactose solutions (resp. tests 3 through 10 of the present invention), in aqueous saturated cyclodextrin β solutions—that is 0.19 M in glucose units (comparative test 11) and of 0.5 M, 2 M and 2.5 M α-methylglucoside aqueous solutions (resp. tests 12 through 14 of the present invention).

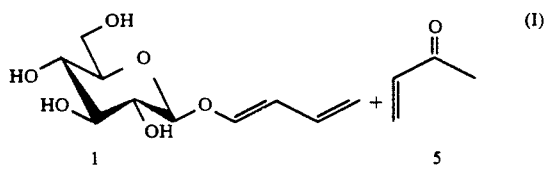

Cyclodextrin β was obtained from Janssen Chimica Co.

Table I below lists the values of the second order reaction rate $k \times 10^5/M^{-1}s^{-1}$ for each test for the particular reaction at 25° C. with each of the cited additives.

As shown by Table I, compared to pure water, the reaction is decelerated by the presence of a simple alcohol (methanol) whereas it is accelerated by aqueous solutions of carbohydrates.

Again as shown by Table I (comparison of tests 5, 6 and 11), surprisingly, glucose already at a concentration of 2 M introduces higher acceleration than a saturated solution of cyclodextrin β known to accelerate the Diels-Alder reactions by forming hydrophobic diene accumulation and dienophil in its hydrophobic cage.

TABLE I

| Test | Additive | $k \times 10^5/M^{-1}s^{-1}$ |
|---|---|---|
| 1 (comparison) | none (H$_2$O) | 28.2 |
| 2 (comparison) | MeOH 50% | 7.5 |
| 3 | 0.5M glucose | 29.8 |
| 4 | 1M glucose | 34.8 |
| 5 | 2M glucose | 44.6 |
| 6 | 3M glucose | 61.3 |
| 7 | 0.5M saccharose | 32 |
| 8 | 2M ribose | 35.1 |
| 9 | 1M mannose | 32.5 |
| 10 | 1M galactose | 34.2 |
| 11 (comparison) | 0.19M glucose units saturated cyclodextrin β solution | 41.6 |
| 12 | 0.5M α-methylglucoside | 30.9 |
| 13 | 2M α-methyglucoside | 43.7 |
| 14 | 2.5M α-methylglucoside | 48.1 |

3 M concentration glucose introduces a gain of 117% in reaction rate compared to pure water and 47% compared to a saturated solution of cyclodextrin β.

Example 2

The Diels-Alder reaction between 1-β-D-glucosyl-1-3-butadiene and butenone was carried out at 25° C. at atmospheric pressure in reaction media consisting of aqueous solutions containing from 0 to 10% molar of glucose in order to determine the variation of the second order rate constant as a function of glucose concentration. No measurable acceleration was detected for reaction media consisting of aqueous glucose solutions up to 0.2 M.

The attached FIG. 1 shows the function $\text{Ln}(k_{obs}/k_{water})$ in relation to the glucose concentration in the 0.5–3 M interval; the function is a straight line.

For very high glucose concentrations (3.5 M), no increase in reaction acceleration was observed relative to a 3 M solution.

The attached FIG. 2 shows the variation of $\text{Ln}(k_{obs}/k_{water})$ in relation to the concentration of α-methylglucoside; this function is a straight line.

Example 3

(comparison)

In order to ascertain any effect of solution viscosity on the reaction rate considered (25° C., atmospheric pressure), the second-order rate constants were measured in a 2.6 m glucose solution and in polyethylene glycol solutions (PEG 6000 from Janssen Chimica Co.) of similar viscosity as and of higher viscosity than that of said glucose solution. Table II below lists the results.

TABLE II

| | H$_2$O | glucose (2.6 m) | PEG 6000 (70 g/l) | PEG 6000 (140 g/l) |
|---|---|---|---|---|
| viscosity (cP) | 0.9426 | 2.845 | 2.527 | 5.507 |
| $k \times 10^5/M^{-1}s^{-1}$ | 28.2 | 44.9 | 25.5 | 23 |

As shown by Table II, PEG 6000, contrary to glucose, retards the reaction and the deceleration effect increases as viscosity increases.

Example 4

The Diels-Alder reaction between methoxybutadiene (6) and butenone (5) [reaction II] is carried out in this Example at 25° C. and atmospheric pressure in pure water

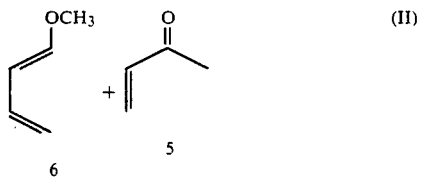

(comparison test 15), in a 50% aqueous MeOH solution (comparison test 16), in 0.5 M, 1 M, 1.5 M, 4 M glucose solutions, in 0.5 M, 1 M, 2 M saccharose solutions, in 1 M, 2 M, 3 M ribose solutions (resp, test 17 through 26 of the present invention), and in saturated cyclodextrin β, that is 0.19 M glucose units (comparison test 27).

The cyclodextrin β was provided by Janssen Chimica Co.

Table III below lists the values of the second -order rate constant $k \times 10^5/M^{-1}s^{-1}$ for each of the tests for the particular reaction with each of the cited additives.

The attached FIG. 3 shows the variation of $Ln(k_{obs}/k_{water})$ as a function of the concentration of saccharose, glucose, ribose for reaction (II) of the present Example 4 and also as a function of glucose for the reaction (I) of Example 1 above.

TABLE III

| Test | Additive | $k \times 10^5/M^{-1}s^{-1}$ |
|---|---|---|
| 15 (comparison) | none (H$_2$O) | 109 |
| 16 | MeOH 50% | 23.4 |
| 17 | 0.5M glucose | 117 |
| 18 | 1M glucose | 133 |
| 19 | 1.5M glucose | 154 |
| 20 | 4M glucose | 300 |
| 21 | 0.5M saccharose | 123 |
| 22 | 1M saccharose | 152 |
| 23 | 2M saccharose | 230 |
| 24 | 1M ribose | 124 |
| 25 | 2M ribose | 137 |
| 26 | 3M ribose | 166 |
| 27 (comparison) | cyclodextrin β solution saturated 0.19M in glucose units | 254 |

The comparison of Example 1 and Example 4 shows that all the claimed carbohydrates raise the reaction rate whereas methanol decreases it.

Be it noted that the glucose effect is similar in both reactions (I) and (II)—the straight lines denoting $Ln(k_{obs}/k_{water})$ as a function of glucose concentration in each reaction practically coincide.

Furthermore in both reactions I and II, concentrated glucose introduces significantly higher acceleration than a saturated cyclodextrin solution.

Again in terms of molarity, saccharose raises the reaction rate more than glucose which in turn raises it more than ribose.

The above Examples illustrate certain behaviors of the novel chiral reaction medium of the invention whereby it is possible to substantially increase the rate of organic reactions in simple and economic manner without incurring toxic problems.

We claim:

1. Process for conducting an organic reaction so that the rate of said organic reaction is increased comprising conducting said organic reaction in an aqueous concentrated solution of at least one carbohydrate selected from the group consisting of monosaccharides, disaccharides and trisaccharides and their alkylglycosides of which the alkyl group contains from 1-4 carbon atoms, wherein said aqueous concentrated solution acts as a chiral reaction medium for said organic reaction.

2. Process according to claim 1 wherein said carbohydrate is glucose.

* * * * *